United States Patent
Heng et al.

(10) Patent No.: US 8,609,363 B2
(45) Date of Patent: Dec. 17, 2013

(54) VIABILITY CELL COUNTING BY DIFFERENTIAL LIGHT ABSORPTION

(75) Inventors: Xin Heng, Hercules, CA (US); Eugene Breniman, Martinez, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/298,682

(22) Filed: Nov. 17, 2011

(65) Prior Publication Data

US 2012/0295300 A1 Nov. 22, 2012

Related U.S. Application Data

(60) Provisional application No. 61/414,947, filed on Nov. 18, 2010.

(51) Int. Cl.
*C12Q 1/02* (2006.01)
*C12Q 1/00* (2006.01)

(52) U.S. Cl.
USPC .................................. 435/29; 435/4

(58) Field of Classification Search
USPC ........................................ 435/4, 29
See application file for complete search history.

(56) References Cited

U.S. PATENT DOCUMENTS

| 7,411,680 B2 | 8/2008 | Chang et al. |
| 2002/0071121 A1 | 6/2002 | Ortyn |
| 2006/0223165 A1 | 10/2006 | Chang et al. |
| 2007/0195391 A1 | 8/2007 | Nishikawa et al. |
| 2008/0068476 A1 | 3/2008 | Yun |
| 2008/0182290 A1 | 7/2008 | Flugelman |

OTHER PUBLICATIONS

Ren et al. Continuous Intact Cell Detection and Viability Determination by CE With Dual Wavelength Detection; Electrophoresis, vol. 31 (2010) pp. 324-330.*
Strober, W. Trypan Blue Exclusion Test of Cell Viability; Current Protocols in Immunology (1997) A.3B.1-A.3B.2.*
International Search Report and Written Opinion for PCT/US11/61363, mailed on Mar. 12, 2012, 17 pages.
U.S. Appl. No. 12/869,979, filed Aug. 27, 2010 (24 pages).

* cited by examiner

*Primary Examiner* — Susan Hanley
*Assistant Examiner* — Paul Martin
(74) *Attorney, Agent, or Firm* — Kilpatrick Townsend & Stockton LLP.

(57) ABSTRACT

Cell counts that distinguish between live and dead cells while providing an accurate count of the total of live and dead cells are obtained by the use of a vital stain in conjunction with illumination of the cell population and the taking of light images at different wavelengths, one which is not absorbed by the stain and one that is absorbed by the stain. Masking and inaccuracies in the counting of dead cells is thereby avoided.

20 Claims, No Drawings

VIABILITY CELL COUNTING BY DIFFERENTIAL LIGHT ABSORPTION

CROSS-REFERENCE TO RELATED APPLICATIONS

This application claims the benefit of U.S. Provisional Patent Application No. 61/414,947, filed Nov. 18, 2010, the contents of which are incorporated herein by reference.

BACKGROUND OF THE INVENTION

1. Field of the Invention

This invention lies in the field of hemocytometry and systems in general for the counting of cells in biological tissue or fluids.

2. Description of the Prior Art

The ability to distinguish between live cells and dead cells in biological tissue or fluid offers information of value in both diagnostics and research. The distinction is of value in assessing microbial infestations, for example, since only the live cells in a microbial population possess metabolic and reproductive activity, and when the cells are pathogenic microorganisms, only the live cells present a potential health risk. The distinction is also of value in investigations of the efficacy or mechanism of action of drugs and pharmaceuticals, since determinations of cell viability or death are often a part of such investigations. Live cells must also be distinguished from dead cells in certain lines of research that involve investigations of morphological characteristics of cells, since the results of these investigations can be obscured when the characteristics of interest are masked by phenotypic characteristics of dead cells.

One means of distinguishing between live and dead cells is by assaying for DNA, since DNA is commonly associated only with live cells. This method is not reliable, however, since DNA can persist in a cell for several weeks after cell death. Other methods include capturing images of cells that have been treated with a contrast agent that associates with a marker that is present in only live or only dead cells. The treatment is an extra step, however, and is not one that automated instruments that are currently in existence can be readily adapted to incorporate. Still further methods include the use of vital stains that cause dead cells to absorb incident light and that thereby allow one to eliminate dead cells from the total cell count. When dead cells are treated with vital stains, however, the outlines of the cells are often indiscernible and multiple cells that overlap or abut each other can be miscounted as single cells, while single cells of irregular shapes can be mistaken as two or more cells. Live cells are relatively easy to differentiate from each other, even when they are in clumps or of dissimilar sizes, because live cells have bright cores and dark contours, resulting in contrast between the cores and the cell outlines that permits individual cell recognition by computer software or the human brain. No such contrast is present in dead cells since both the cell interiors and the cell contours are dark. The declumping of dead cells for counting purposes is therefore nearly impossible. Certain cell counters presently available from commercial suppliers have a large field of view in combination with limited resolution. Together, these features make it difficult to differentiate live cells from dead cells, and the difficulty is aggravated when the dead cells are clumped together.

SUMMARY OF THE INVENTION

It has now been discovered that cell counts that distinguish between live cells and dead cells in a cell population can be obtained by treating the population with a vital stain, illuminating the population or an aliquot of the population, and taking as few as two images of light from the illumination that penetrates the population. The images are of light from different wavelength bands that are absorbed by the vital stain to different degrees. One image allows the user or a sensor to count, or to achieve a count representative of, all cells, live and dead, while the other image allows the user or a sensor to distinguish live cells from dead cells, or to achieve a count representative of live cells as distinct from dead cells. Distinguishable images, preferably successive images, of the cells are obtained from the two illuminations, and the two images collectively provide full information regarding both the live and the dead cells. In particular, the image of light with the lesser degree of absorption by the cell population, which can be an image of light that is substantially unabsorbed by the population, permits the user or a sensor to count, or to achieve a count representative of, all cells, live and dead, while the image of light with the greater degree of absorption permits the user or a sensor to distinguish live cells from dead cells, or to achieve a count representative of live cells as distinct from dead cells. The former image, i.e., the image from which the total cell count is derived, will show individual cells by virtue of contrasting cell outlines rather than inconclusive shapes that would otherwise result from the absorption of incident light. From the two counts, therefore, one can obtain an accurate count for total cells and live cells, respectively, and also of dead cells by subtraction.

DETAILED DESCRIPTION OF THE INVENTION AND SELECTED EMBODIMENTS

The term "vital stain" is used herein to denote stains or dyes that exhibit dye exclusion of live vs. dead cells, i.e., that penetrate membranes of dead cells preferentially over membranes of live cells. Vital stains are known in the art, and any stain, including those known in the art, that exhibits dye exclusion can be used in the practice of this invention. Examples of vital stains are trypan blue, brilliant cresyl blue, methylene blue, trypan red, vital red, neutral red, Janus green, indocyanine green, methylene green, safranin, aniline yellow, carboxyfluorescein diacetate succinimidyl ester, propidium iodide, ethidium bromide, fluorescein diacetate, carboxyfluorescein diacetate, fluorescein isothiocyanate diacetate, and azafloxin. The more common among these are trypan blue, brilliant cresyl blue, methylene blue, trypan red, vital red, neutral red, Janus green, indocyanine green, propidium iodide, and methylene green, particularly trypan blue, brilliant cresyl blue, Janus green, and propidium iodide. A subset of further interest is trypan blue, brilliant cresyl blue, methylene blue, Janus green, and propidium iodide. In many situations, trypan blue and propidium iodide will be the most convenient, and trypan blue alone is favored for certain implementations. Combinations of vital stains can be used to achieve particular absorption profiles, but in most cases a single vital stain will provide results sufficient to achieve the distinctions sought herein.

As noted above, the desired cell counts can be obtained with as few as two images at different wavelength bands, although the counts can also be obtained with three or more such images of differing wavelength bands. In one image, cells whose membranes have been penetrated by the stain will be distinguishable from cells whose membranes have not been penetrated, and in another image cells whose membranes have been penetrated by the stain will not be distinguishable from cells whose membranes have not been penetrated. Images that are distinguishable from each other by the human eye as well as images that are distinguishable by instrumentation are all within the scope of this invention. In many cases, the image representing the greater absorption is an image of light that is entirely, as opposed to partially, absorbed by the vital stain such that no light at all is either transmitted to the imager or scattered by those cells that stain has penetrated. Differences in degrees of absorption can be more accurately detected in some cases by instrumentation than by the naked eye. In most cases, the distinction between absorption and nonabsorption will be determined by the detection limits of the observer or the instrument. The wavelength spectrum of a given illumination can be a single absorption peak, a series of two or more such peaks, broad peaks or narrow peaks, peaks with extended tails, or combinations of such peaks. Differences in absorption can be enhanced by optical filters, or by the use of single-color LEDs, or by other means that limit the detection to selected segments of the spectrum.

The image generated by light that has not been absorbed by the vital stain can be obtained by transmission of the light through the cell population or by the scattering of light by the cell population. Scattering images can be obtained by dark field microscopy. Regardless of whether the nonabsorption image is obtained by transmission or scattering, the differentiation between the image representing absorption and non-absorption can be achieved in any of various ways. In certain embodiments of the invention, each image can be obtained by use of a separate illumination at a wavelength band different from those of the other illumination(s). In these embodiments, the wavelength band for each image will be controlled by the wavelength band of the illumination, and the image itself can be of either a portion of the illumination light transmitted through or scattered by the cell population or all of light so transmitted or scattered. The wavelength band of the image is thus determined by the illumination. In other embodiments, the wavelength band for each image will be controlled by limiting the wavelength band that reaches the detector, or is detected by the detector, without so limiting the wavelength band of the illumination. This can be accomplished either by a detector that selects only light of a designated wavelength band for detection, or by interposing a filter between the cell population and the detector.

The image wavelengths will be chosen in conjunction with the choice of vital stain to achieve the desired difference in degrees of absorption. In the example of trypan blue as the vital stain, the image representing a lack of absorption or the lesser or minimal absorption can be an image of blue light, since trypan blue has very low absorption of light in the blue range. Thus, depending on whether wavelength discrimination is achieved in the illumination or detection, either the cell population can be illuminated with blue light alone or with light of a broader spectrum while a blue light filter is placed between the cell population and the detector. Alternatives to blue light that are likewise unabsorbed, i.e., transmitted or scattered, by trypan blue are infrared light and ultraviolet light. From the image of unabsorbed light, one can achieve a count representing all cells, live and dead. The image representing absorption or a higher degree of absorption than the non-absorption image can then be achieved with any light that includes wavelengths outside of the blue range as a substantial part of the spectrum. Examples of light to be absorbed by trypan blue, i.e., light that includes a substantial portion of wavelengths outside the blue range, are red light, orange light, and white light. Orange light is noted in view of its wavelength of approximately 590 nm, which coincides with an absorption peak of trypan blue. The image from this second illumination permits counting of the live cells.

The images can be taken in succession, in which case the order in which the images are taken is not critical. Thus, the non-absorptive, or lesser absorptive, image can be performed either before or after the image representing absorption by the vital stain, or vice versa. Depending on where in the optical path the wavelength discrimination is imposed, illumination can be achieved by a conventional light source, such as a white light source, or by a white light source in conjunction with color filters, or by a multicolor light-emitting diode (LED). The choice of light source is not critical and can vary widely. One type of a light source is a single white light-emitting diode (LED) with a fluorescent coating. An example is LUXEON® Rebel White, part no. LXML-PWN1-0050, available from Philips Lumileds Lighting Company, San Jose, Calif., USA. Illumination can be either by trans-illumination or epi-illumination, although trans-illumination will be more convenient in many instrument configurations. Illumination can be performed through a collimating lens.

The image can be either an analog image or a digital image. In certain embodiments, digital images are preferred. Images can be obtained by sensors of various types known in the art. Examples are charge-coupled devices (CCDs), complementary metal oxide semiconductors (CMOS), photodiode arrays, charge injection devices, liquid-crystal-on-silicon imagers, and high-temperature poly-silicon imagers. CCDs and CMOS detectors are particularly convenient for digital imaging. A CMOS image sensor having pixels that are selectively responsive to different wavelengths can be used to form the different images, and such a sensor can be particularly useful when illumination is performed with a wavelength band that encompasses the wavelength bands of all of the images to be taken. Such illumination of course can be achieved with white light and without the need for filters. Thus, for a two-image system, certain pixels of the sensor will be responsive to wavelengths within the wavelength band of one image and other pixels will be responsive to wavelengths within the wavelength band of the other image.

Digital images can be processed by any pattern recognition program, including programs readily compiled by those skilled in the art and commercially available software. An open-source example of such a program is ImageJ, a Java-based image processing program developed at the National Institutes of Health and reported by Collins, T. J., "ImageJ for microscopy," *BioTechniques* 43 (1 Suppl.): 25-30 (July 2007). The use of ImageJ in hematology systems is reported by Gering, T. E., and C. Atkinson, "A rapid method for counting nucleated erythrocytes on stained blood smears by digital image analysis," *J. Parasitol.* 90(4): 879-81 (2004). By adding a second illumination wavelength that provides image contrast to dead cells, cell counting systems of the present invention have an additional degree of freedom, and the change in the image contrast allows a new classifier to be added to the image analysis software. Cells in one image are compared to the same cells (i.e., cells at the same location) in the second image. If the contrast in a given cell between the two images differs by more than a threshold value, the cell is identified as a dead cell, whereas if there is no difference or a difference lower than the threshold, the cell is identified as a live cell. The threshold can be pre-determined or set by comparing images of cells known to be alive with cells known to be dead. A mathematical analysis known in the art as a discriminant analysis can be applied to the images to separate cells of one contrast class from those of another contrast class.

Illumination and imaging in accordance with this invention are particularly suitable for automated cell counters. Descriptions of automated cell counters are found in Chang, J. K., et al., U.S. Pat. No. 7,411,680 B2, issued Aug. 12, 2008, "Device for Counting Micro Particles," Chang, J. K., et al., United States Patent Application Publication No. US 2006/0223165 A1, published Oct. 5, 2006, "Device for Counting Cells and Method for Manufacturing the Same," and co-pending U.S. patent application Ser. No. 12/869,979, filed Aug. 27, 2010, entitled "Compact Automated Cell Counter," inventors McCollum et al. (Bio-Rad Laboratories, Inc., assignee).

Cells that can be counted in accordance with the present invention include both adherent cells and non-adherent cells, and the non-adherent cells can be cells in suspension, cells in biological tissue, cells in a growth medium, plated cells, or cells in any other form. Examples of cells that can be counted by the methods disclosed herein are erythrocytes, leukocytes, thrombocytes, liver or liver-derived cells including primary hepatocytes and liver epithelial cells, epithelial cells in general, endothelial cells in general, neuronal cells, mesenchymal cells, pancreatic cells, skeletal muscle cells, cardiomyocytes, carcinoma-derived cells, bone marrow cells, islets of Langerhans, adrenal medulla cells, osteoblasts, osteoclasts, T-lymphocytes, neurons, glial cells, ganglion cells, retinal cells, and myoblast cells. Stem cells can also be used; examples are mesenchymal stem cells, neuronal stem cells, induced pluripotent stem cells, hematopoietic stem cells, mouse embryonic stem cells, and human embryonic stem cells. Many other examples exist and will be readily apparent to those of skill in the art.

In the claims appended hereto, the terms "a" and "an" are intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for counting cells in a cell population to distinguish between live cells and dead cells, said method comprising:
   (a) treating an aliquot of said population with a vital stain that penetrates dead cells preferentially over live cells;
   (b) illuminating said aliquot so treated with light of a first wavelength band and forming a first image of said aliquot, wherein light of said first wavelength band is substantially unabsorbed by said vital stain and allows both live and dead cells to be visualized;
   (c) counting both live and dead cells in said first image;
   (d) illuminating said aliquot so treated with light of a second wavelength band and forming a second image of said aliquot, wherein light of said second wavelength band is at least partially absorbed by said vital stain;
   (e) counting, in said second image, live cells that have not been substantially penetrated by said vital stain; and
   (f) subtracting the number of live cells counted in said second image from the number of live and dead cells counted in said first image to obtain the number of dead cells in said first image,
   wherein counting cells in the first and second images comprises detecting contrast between the interiors and outlines of cells.

2. The method of claim 1 wherein step (b) comprises illuminating said aliquot with a first illumination using light limited to said first wavelength band and forming said first image of said aliquot from said first illumination,
   and wherein step (d) comprises separately illuminating said aliquot with a second illumination using light limited to said second wavelength band and forming said second image of said aliquot from said second illumination.

3. The method of claim 2 wherein said vital stain is trypan blue, said light of said first illumination is a member selected from the group consisting of blue light, infrared light, and ultraviolet light, and said light of said second illumination is a member selected from the group consisting of red light, orange light, and white light.

4. The method of claim 2 wherein said vital stain is trypan blue, said light of said first illumination is blue light, and said light of said second illumination is orange light.

5. The method of claim 1 wherein steps (b) and (d) comprise illuminating said aliquot with light of a wavelength band that encompasses both said first wavelength band and said second wavelength band, step (b) comprises forming said first image using light within said first wavelength band only, and step (d) comprises forming said second image using light within said second wavelength band only.

6. The method of claim 5 wherein said light of a wavelength band that encompasses both said first wavelength band and said second wavelength band is white light.

7. The method of claim 5 comprising forming said first image through an absorption filter that passes only light within said first wavelength band, and forming said second image through an absorption filter that passes only light within said second wavelength band.

8. The method of claim 5 comprising forming said first and second images by a CMOS image sensor having pixels selectively responsive to wavelengths within said first wavelength band separate from pixels selectively responsive to wavelengths within said second wavelength band.

9. The method of claim 1 wherein said vital stain is a member selected from the group consisting of trypan blue, brilliant cresyl blue, methylene blue, trypan red, vital red, neutral red, Janus green, indocyanine green, methylene green, safranin, aniline yellow, carboxyfluorescein diacetate succinimidyl ester, propidium iodide, ethidium bromide, fluorescein diacetate, carboxyfluorescein diacetate, fluorescein isothiocyanate diacetate, and azafloxin.

10. The method of claim 1 wherein said vital stain is a member selected from the group consisting of trypan blue, brilliant cresyl blue, methylene blue, trypan red, vital red, neutral red, Janus green, indocyanine green, and methylene green.

11. The method of claim 1 wherein said vital stain is a member selected from the group consisting of trypan blue, brilliant cresyl blue, Janus green, and propidium iodide.

12. The method of claim 1 wherein said vital stain is a member selected from the group consisting of trypan blue and propidium iodide.

13. The method of claim 1 wherein said vital stain is trypan blue.

14. The method of claim 1 wherein said first image is formed from light transmitted through said aliquot.

15. The method of claim 1 wherein said first image is formed from light scattered by said aliquot.

16. The method of claim 1 wherein said first and second images are digital images.

17. The method of claim 1 comprising forming said first and second images on a member selected from the group consisting of a charge-coupled device, a complementary metal oxide semiconductor, a photodiode array, a charge injection device, a liquid-crystal-on-silicon imager, and a high-temperature poly-silicon imager.

18. The method of claim 1 comprising forming said first and second images on a member selected from the group consisting of a charge-coupled device and a complementary metal oxide semiconductor.

19. The method of claim 1 comprising forming said first and second images on a complementary metal oxide semiconductor.

20. A method for counting cells in a cell population to distinguish between live cells and dead cells, said method comprising:
(a) treating an aliquot of said population with a vital stain that penetrates dead cells preferentially over live cells;
(b) illuminating said aliquot so treated with light of a first wavelength band and forming a first image of said aliquot;
(c) illuminating said aliquot so treated with light of a second wavelength band and forming a second image of said aliquot,
wherein said first wavelength band and said second wavelength band are selected such that said vital stain absorbs substantially more light from said second wavelength band than from said first wavelength band; and
(d) for individual cells in said aliquot, detecting the difference in contrast between said first image and said second image, and comparing said difference to a threshold value selected such that cells exhibiting contrast differences above said threshold value are defined as dead cells and cells exhibiting contrast differences below said threshold value are defined as live cells, and counting said cells defined as dead cells separately from said cells defined as live cells.

* * * * *